(12) United States Patent
Lehtonen et al.

(10) Patent No.: US 11,433,156 B2
(45) Date of Patent: Sep. 6, 2022

(54) INSTRUMENT CASSETTE FOR HANDLING INSTRUMENTS

(71) Applicant: LM-INSTRUMENTS OY, Parainen (FI)

(72) Inventors: Kari Lehtonen, Parainen (FI); Gaius Voltti, Parainen (FI)

( * ) Notice: Subject to any disclaimer, the term of this patent is extended or adjusted under 35 U.S.C. 154(b) by 434 days.

(21) Appl. No.: 16/630,230

(22) PCT Filed: Jul. 5, 2018

(86) PCT No.: PCT/FI2018/050532
§ 371 (c)(1),
(2) Date: Jan. 10, 2020

(87) PCT Pub. No.: WO2019/012182
PCT Pub. Date: Jan. 17, 2019

(65) Prior Publication Data
US 2020/0129653 A1    Apr. 30, 2020

(30) Foreign Application Priority Data

Jul. 12, 2017   (FI) ...................................... 20175680

(51) Int. Cl.
*A61L 2/07* (2006.01)
*A61L 12/00* (2006.01)
*A61B 50/20* (2016.01)

(52) U.S. Cl.
CPC .............. *A61L 12/00* (2013.01); *A61B 50/20* (2016.02); *A61L 2/07* (2013.01); *A61L 2202/182* (2013.01); *A61L 2202/24* (2013.01)

(58) Field of Classification Search
CPC ... A61L 2/06; A61L 2/07; A61L 12/00; A61L 2202/24; A61L 2202/182; A61B 50/20; A61B 50/22; A61B 50/33
USPC ....... 206/363, 364, 368–370, 438, 561, 564, 206/565
See application file for complete search history.

(56) References Cited

U.S. PATENT DOCUMENTS

| 4,643,303 | A | * | 2/1987 | Arp | ........................... | A61L 2/26 206/370 |
| 4,959,199 | A | | 9/1990 | Brewer | | |
| 5,215,726 | A | * | 6/1993 | Kudla | ....................... | A61L 2/26 206/370 |

(Continued)

FOREIGN PATENT DOCUMENTS

WO    2015080578 A1    6/2015

*Primary Examiner* — Luan K Bui
(74) *Attorney, Agent, or Firm* — Fay Sharpe LLP

(57) ABSTRACT

An instrument cassette (100) for handling instruments (111) comprises support structures (101) for mechanically supporting the instruments (111), and a shielding structure (102, 103) for containing operational portions (112) of the instruments (111) so that a risk of unintentional touching the operational portions (112) is reduced. At least one wall (104) of the shielding structure (103) comprises channels (105) for allowing liquid and gaseous substances to flow through the wall. The substances may comprise for example hot vapor used in an autoclaving sterilization process. The channels (105) are shaped to prevent the operational portions (112) of the instruments (111) from protruding through the wall (104) via the channels (105). Thus, there is no need for a high number of very small channels which may be difficult to manufacture in a cost effective way.

19 Claims, 2 Drawing Sheets

(56) References Cited

U.S. PATENT DOCUMENTS

| | | | | |
|---|---|---|---|---|
| 5,294,413 A * | 3/1994 | Riihimaki | ............... | A61L 2/06 |
| | | | | 206/370 |
| 5,384,103 A * | 1/1995 | Miller | ............... | A61L 2/26 |
| | | | | 206/508 |
| 5,720,930 A * | 2/1998 | Bean | ............... | A61L 2/26 |
| | | | | 428/167 |
| 5,725,097 A * | 3/1998 | Bettenhausen | ............... | A61L 2/26 |
| | | | | 292/210 |
| 7,544,336 B2 * | 6/2009 | Powell | ............... | A61L 2/26 |
| | | | | 206/370 |
| 9,084,834 B1 * | 7/2015 | Meuchel | ............... | E05C 1/04 |

* cited by examiner

INSTRUMENT CASSETTE FOR HANDLING INSTRUMENTS

FIELD OF THE DISCLOSURE

The disclosure relates to an instrument cassette for handling instruments which can be, for example but not necessarily, medical or dental hand instruments. The instrument cassette can be used for holding instruments for example when the instruments are sterilized by autoclaving.

BACKGROUND

In many cases, instruments are handled with the aid of instrument cassettes each of which is suitable for holding a set of instruments during e.g. an autoclaving sterilization process. Instruments placed in an instrument cassette may comprise for example medical and/or dental hand instruments needed for carrying out given measures. An instrument cassette comprises typically support structures for mechanically supporting the instruments so that the instruments are adjacent to each other. Furthermore, the instrument cassette may comprise shielding structures for containing operational portions of the instruments so that a risk of unintentional touching the operational portions is reduced. In this document, the phrase "operational portion" means a part of an instrument for performing the operations according to the purpose of use of the instrument. An operational portion can be e.g. a blade of a knife. The above-mentioned shielding structures comprise channels for allowing liquid and gaseous substances to flow through the shielding structures and thereby to get in contact with the operational portions of the instruments. The above-mentioned substances may comprise for example hot vapor used in an autoclaving sterilization process.

An inherent challenge related to an instrument cassette of the kind described above is that, on one hand, the shielding structures should be sufficiently open for allowing liquid and gaseous substances to flow through the shielding structures but, on the other hand, the shielding structures should be sufficiently closed to reduce the risk of unintentional touching the operational portions. Furthermore, in a case where an operational portion of an instrument is a sharp spike having a bend, there is a risk that the operational portion protrudes through a shielding structure via one of the channels of the shielding structure. A straightforward approach to prevent operational portions of instruments from protruding through the shielding structures is to make the channels sufficiently small. This approach however leads to a situation where the number of the channels has to be high and thereby isthmuses between the channels have to be narrow in order to provide a sufficient flow area for liquid and gaseous substances through the shielding structures. An instrument cassette is typically made of plastic such as e.g. polyphenylene sulfide "PPS", and narrow isthmuses of plastic can be mechanically weak and susceptible to damages. Another straightforward approach is to provide the channels of the shielding structure with sufficiently dense grids of thin metal wires. This approach, however, complicates the manufacturing of an instrument cassette and increases the manufacturing costs of the instrument cassette.

SUMMARY

The following presents a simplified summary in order to provide a basic understanding of some embodiments of the invention. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In this document, the word "geometric" when used as a prefix means a geometric concept that is not necessarily a part of any physical object. The geometric concept can be for example a geometric point, a geometric line, a geometric plane, a non-planar geometric surface, a geometric room, or any other geometric entity that is zero, one, two, or three dimensional.

In accordance with the invention, there is provided a new instrument cassette for handling instruments such as for example medical or dental hand instruments.

The instrument cassette comprises:
support structures for mechanically supporting the instruments, and
at least one shielding structure for containing operational portions of the instruments and for reducing a risk of unintentional touching the operational portions of the instruments.

At least one wall of the shielding structure comprises channels for allowing liquid and gaseous substances, e.g. hot vapor used in an autoclaving sterilization process, to flow through the wall. The wall can be for example the bottom of the shielding structure. The channels are shaped so that a straight and unbending round rod having a diameter more than 1.5 mm is incapable of penetrating the wall via the channels when the straight and unbending round rod is perpendicular to a geometric plane parallel with the wall so as to prevent the operational portions of the instruments from protruding through the wall via the channels, and so that a bendable round rod having a diameter more than 1.5 mm is capable of penetrating the wall via the channels so as to provide sufficient cross-sectional flow area for the liquid and gaseous substances. The channels can be, for example but not necessarily, inclined with respect to a geometric plane parallel with the wall so that the channels are directed slantingly away from the support structures so as to prevent the operational portions of the instruments from protruding through the wall via the channels. Thus, there is no need for a high number of small channels or for dense grids of thin metal wires on the channels because the channels are shaped in the above-mentioned way.

A number of exemplifying and non-limiting embodiments are described in accompanied dependent claims.

Various exemplifying and non-limiting embodiments both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of un-recited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments and their advantages are explained in greater detail below in the sense of examples and with reference to the accompanying drawings, in which.

DESCRIPTION OF EXEMPLIFYING AND NON-LIMITING EMBODIMENTS

The specific examples provided in the description below should not be construed as limiting the scope and/or the applicability of the accompanied claims. Lists and groups of examples provided in the description are not exhaustive unless otherwise explicitly stated.

Figure 1A:
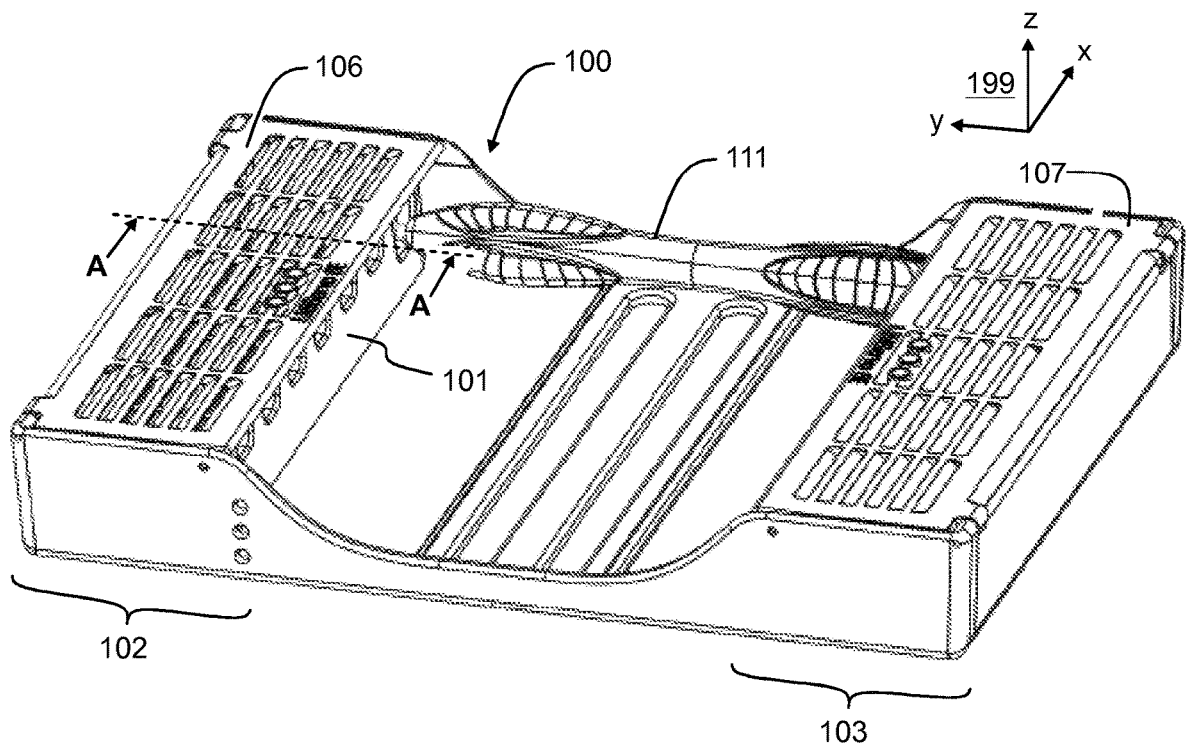
FIGS. 1a and 1b illustrate an instrument cassette according to an exemplifying and non-limiting embodiment.
Figure 1B:
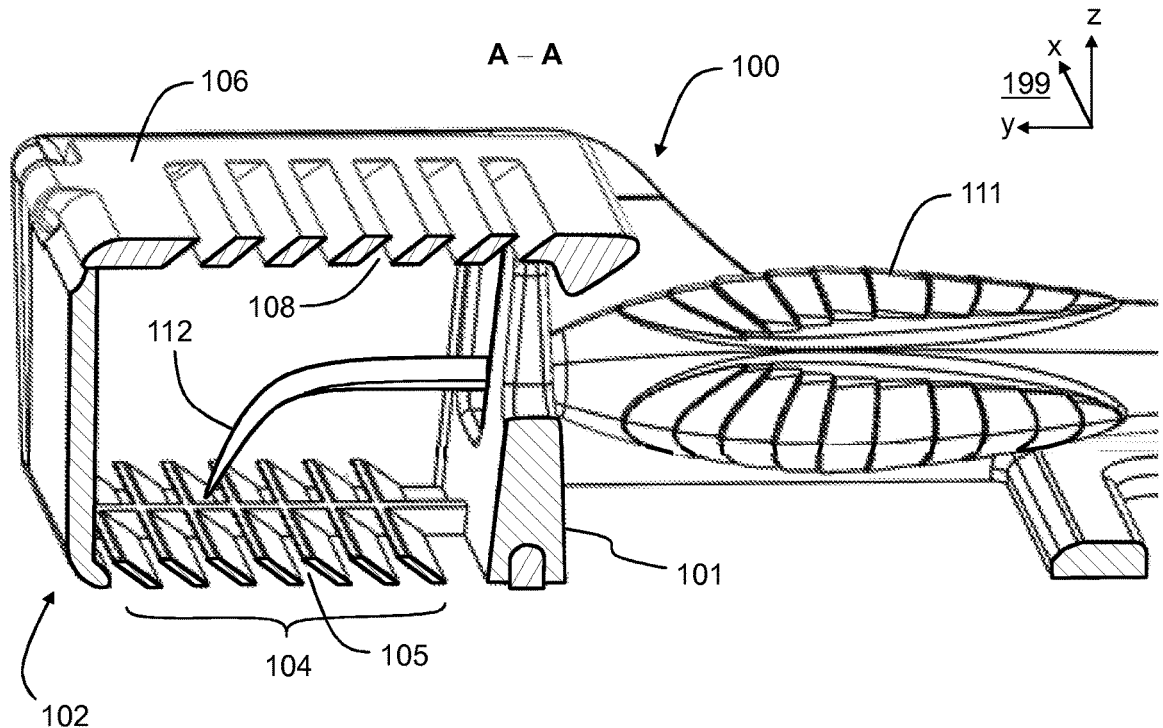

FIGS. 1a and 1b illustrate an instrument cassette 100 according to an exemplifying and non-limiting embodiment. FIG. 1a shows an isometric view of the instrument cassette 100, and FIG. 1b shows a view of a section taken along a line A-A shown in FIG. 1a. The section plane related to FIG. 1b is parallel with the yz-plane of a coordinate system 199. The instrument cassette 100 comprises support structures 101 for mechanically supporting instruments such as e.g. medical or dental hand instruments. In the exemplifying situation shown in FIGS. 1a and 1b, there is an exemplifying instrument 111 in the instrument cassette 100. The instrument cassette 100 comprises shielding structures 102 and 103 for containing operational portions of the instruments and for reducing a risk of unintentional touching the operational portions of the instruments. The operational portion of each instrument is a part of the instrument for performing the operations according to the purpose of use of the instrument. An operational portion can be for example a blade of a knife. The exemplifying instrument cassette 100 comprises the shielding structures 102 and 103 at its both ends, and therefore the instrument cassette 100 is suitable for instruments which have operational portions at both ends. It is, however, also possible that an instrument cassette according to an exemplifying embodiment comprises only one shielding structure, and thus is suitable for only instruments having an operational portion at one end only. The material of the instrument cassette 100 may comprise for example polyphenylene sulfide "PPS".

The shielding structure 102 is depicted in more details in FIG. 1b. The shielding structure 103 can be similar to the shielding structure 102. A wall 104 of the shielding structure comprises channels for allowing liquid and gaseous substances, e.g. hot vapor used in an autoclaving sterilization process, to flow through the wall 104. In FIG. 1b, one of the channels is denoted with a reference 105. The channels are inclined with respect to a geometric plane parallel with the wall 104 so that the channels are directed slantingly away from the support structures 101, and thereby from the instrument 111, so as to prevent the operational portion 112 of the instrument 111 from protruding through the wall 104 via one of the channels. Thus, there is no need for a high number of small channels or for dense grids of thin metal wires on the channels because the channels are directed in the above-mentioned way. The channels are inclined so much that a straight and unbending round rod having a diameter more than 1.5 mm is incapable of penetrating the wall 104 via the channels when the straight and unbending round rod is perpendicular to a geometric plane parallel with the wall 104. Thus, the operational portions of the instruments are prevented from protruding through the wall 104 via the channels. It is also possible that the channels are inclined so much that geometric lines perpendicular to the geometric plane parallel with the wall 104 are incapable of penetrating the bottom 104 through the inclined channels, i.e. one cannot see through the channels when viewing along a geometric line perpendicular to the wall 104.

Figure 1C:
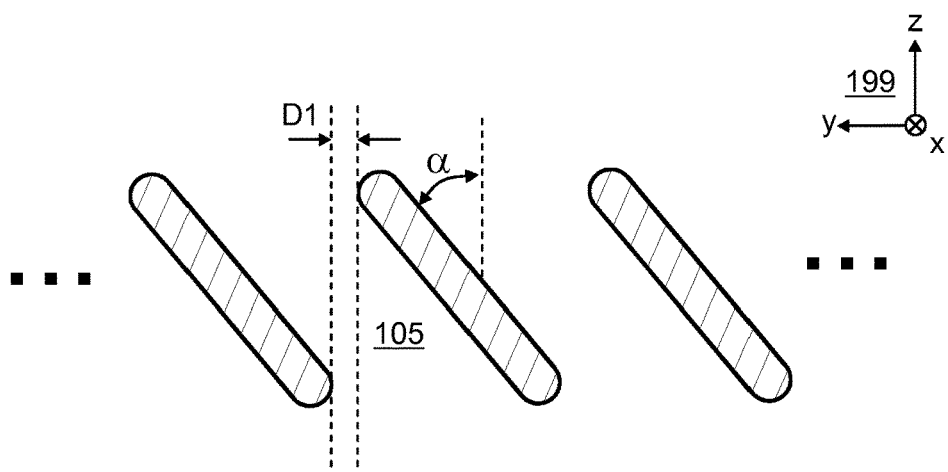
FIGS. 1c and 1d illustrate details of instrument cassettes according to exemplifying and non-limiting embodiments.
Figure 1D:
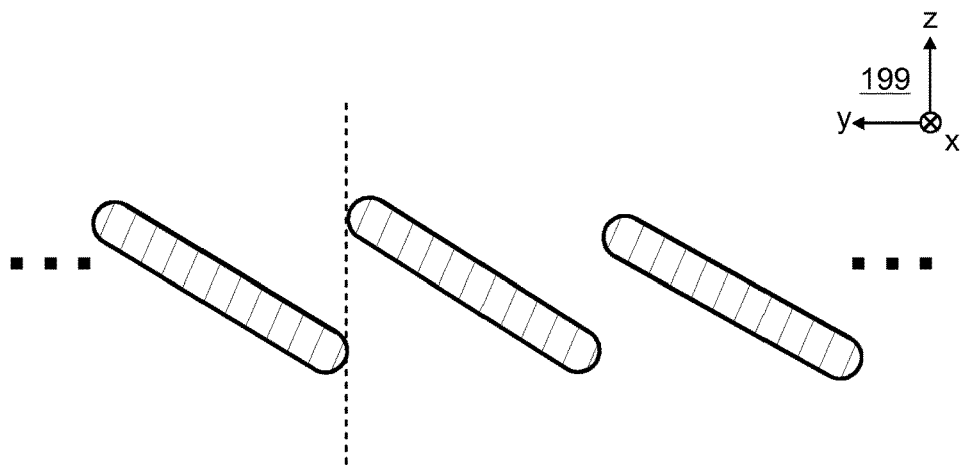
Figure 2:
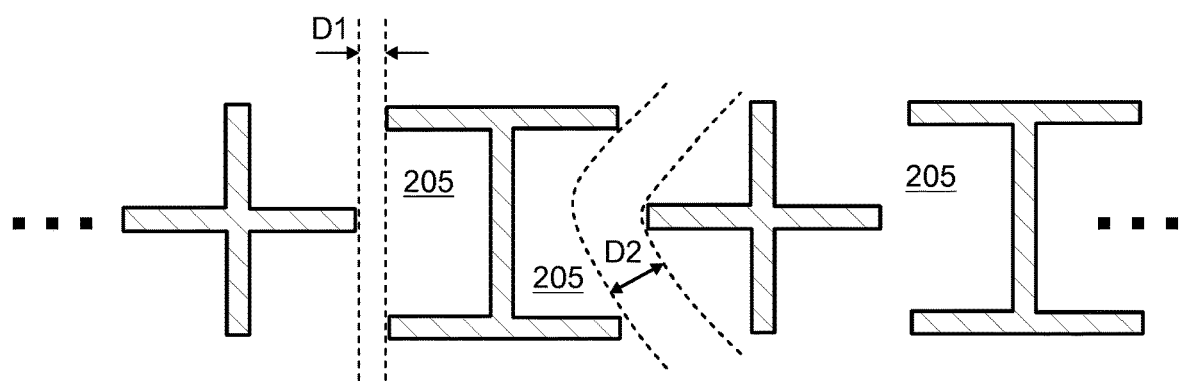
FIG. 2 illustrates a detail of an instrument cassette according to an exemplifying and non-limiting embodiment.

In the exemplifying instrument cassette 100, the wall 104 is a grate that is constituted by flat strips which are parallel with each other, whose lateral directions are inclined with respect to the geometric plane parallel with the wall 104, and which are mechanically supported by strips whose longitudinal directions are substantially perpendicular to the longitudinal direction of the flat strips. FIGS. 1c and 1d illustrate details of the grate in different exemplifying embodiments. In the exemplifying case shown in FIG. 1c, the distance D1 is at most 1.5 mm and thus a straight and unbending round rod having a diameter more than 1.5 mm is incapable of penetrating the wall 104 via the channel 105 when the rod is perpendicular to the wall 104. In the exemplifying case shown in FIG. 1c, each of the channels has an oblong profile when viewed along a geometric line perpendicular to the wall comprising the channels. In the exemplifying case shown in FIG. 1d, the flat strips are arranged so that one cannot see through the channels along a geometric line parallel with the z-axis of the coordinate system 199. The angle α by which the channels are inclined with respect to the z-axis of the coordinate system, i.e. with respect to a geometric line perpendicular to the wall comprising the channels, can be for example from 30 degrees to 70 degrees, or from 40 degrees to 60 degrees, or from 41 degrees to 46 degrees. It is, however, also possible that a corresponding wall of an instrument cassette according to another exemplifying embodiment has a different mechanical construction. FIG. 2 illustrates channels of an instrument cassette according to an exemplifying embodiment. The distance D1 is at most 1.5 mm. Thus, a straight and unbending round rod having a diameter more than D1 is incapable of penetrating the channels 205 when the rod is perpendicular to the wall having the channels. On the other hand, a bendable round rod whose diameter D2 is more than 1.5 mm is capable of penetrating the channels. Thus, a sufficient cross-sectional flow area is provided for liquid and gaseous substances, e.g. for vapor used in an autoclaving process.

In the exemplifying instrument cassette 100, the wall 104 comprising the above-described channels is the bottom of the shielding structure 102. It is, however, also possible that one or more side walls of the shielding structure 102 comprise channels of the kind described above.

The exemplifying instrument cassette 100 further comprises cover elements 106 and 107 for covering the rooms for containing the operational portions of the instruments so as to further reduce the risk of unintentional touching the operational portions. The cover elements 106 and 107 comprise channels for allowing liquid and gaseous substances to flow through the cover elements. The channels of the cover elements can be similar to the channels of the wall 104. In FIG. 1b, one of the channels of the cover element 106 is denoted with a reference 108. As illustrated in FIG. 1b, the channels of the cover element 106 are inclined with respect to a geometric plane parallel with the cover element so that, when the cover element is covering the room for containing the operational portions of the instruments, the channels of the cover element are directed slantingly away from the support structures 101 so as to prevent the operational portions of the instruments from protruding through the cover element via the channels of the cover element. In the exemplifying instrument cassette 100, the cover elements 107 and 108 are hinged to a body section of the instrument cassette 100. It is, however, also possible that a cover element or cover elements is/are shape locked or otherwise mechanically connected to a body section of an instrument cassette according to an exemplifying embodiment. It is also possible that an instrument cassette according to an exemplifying embodiment does not comprise any cover element of the kind mentioned above.

The specific examples provided in the description given above should not be construed as limiting the scope and/or the applicability of the appended claims. Lists and groups of examples provided in the description given above are not exhaustive unless otherwise explicitly stated.

What is claimed is:

1. An instrument cassette for handing instruments, the instrument cassette comprising:
   support structures for mechanically supporting the instruments, and
   at least one shielding structure for containing operational portions of the instruments and for reducing a risk of unintentional touching the operational portions of the instruments,
wherein at least one wall of the shielding structure comprises channels for allowing liquid and gaseous substances to flow through the wall, characterized in that the channels are shaped so that a straight and unbending round rod having a diameter more than 1.5 mm is incapable of penetrating the wall via the channels when the straight and unbending round rod is perpendicular to a geometric plane parallel with the wall so as to prevent the operational portions of the instruments from protruding through the wall via the channels, and a bendable round rod having a diameter more than 1.5 mm is capable of penetrating the wall via the channels so as to provide cross-sectional flow area for the liquid and gaseous substances.

2. An instrument cassette according to claim 1, wherein the channels are inclined with respect to a geometric line perpendicular to the wall so that the channels are directed slantingly away from the support structures so as to prevent the operational portions of the instruments from protruding through the wall via the channels.

3. An instrument cassette according to claim 2, wherein an angle by which the channels, are inclined with respect to the geometric line is at least 30 degrees and at most 70 degrees.

4. An instrument cassette according to claim 1, wherein each of the channels has an oblong profile when viewed along a geometric line perpendicular to the wall.

5. An instrument cassette according to claim 1, wherein the wall comprising the channels is a bottom of the shielding structure.

6. An instrument cassette according to claim 1, wherein the instrument cassette further comprises a cover element for covering a room for containing the operational portions of the instruments so as to further reduce the risk of unintentional touching the operational portions.

7. An instrument cassette according to claim 6, wherein the cover element comprises channels for allowing liquid and gaseous substances to flow through the cover element.

8. An instrument cassette according to claim 7, wherein the channels of the cover element are shaped so that a straight and unbending round rod having a diameter more than 1.5 mm is incapable of penetrating the cover element via the channels of the cover element when the straight and unbending round rod is perpendicular to a geometric plane parallel with the cover element so as to prevent the operational portions of the instruments from protruding through the cover element via the channels of the cover element; and, a bendable round rod having a diameter more than 1.5 mm is capable of penetrating the cover element via the channels of the cover element so as to provide cross-sectional flow area for the liquid and gaseous substances.

9. An instrument cassette according to claim 8, wherein the channels of the cover element are inclined with respect to a geometric plane parallel with the cover element so that, when the cover element is covering the room for containing the operational portions of the instruments, the channels of the cover element are directed slantingly away from the support structures so as to prevent the operational portions of the instruments from protruding through the cover element, via the channels of the cover element.

10. An instrument cassette according to claim 1, wherein material of the instrument cassette comprises polyphenylene sulfide "PPS".

11. An instrument cassette according to claim 2, wherein each of the channels has an oblong profile when viewed along a geometric line perpendicular to the wall.

12. An instrument cassette according to claim 3, wherein each of the channels has an oblong profile when viewed along a geometric line perpendicular to the wall.

13. An instrument cassette according to claim 2, wherein, the wall comprising the channels is a bottom of the shielding structure.

14. An instrument cassette according to claim 3, wherein the wall comprising the channels is a bottom of the shielding structure.

15. An instrument cassette according to claim 4, wherein the wall comprising the channels is a bottom of the shielding structure.

16. An instrument cassette according to claim 2, wherein the instrument cassette further comprises a cover element for covering a room for containing the operational portions of the instruments so as to further reduce the rids of unintentional touching the operational portions.

17. An instrument, cassette according to claim 3, wherein the instrument cassette further comprises a cover element for covering a room for containing the operational portions of the instruments so as to further reduce the risk of unintentional touching the operational portions.

18. An instrument cassette according to claim 4, wherein the instrument cassette further comprises a cover element for covering a room for containing the operational portions of the instruments so as to further reduce the risk of unintentional touching the operational portions.

19. An instrument cassette according to claim 5, wherein the instrument cassette further comprises a cover element for covering a room for containing the operational portions of the instruments so as to further reduce the risk of unintentional touching the operational portions.

* * * * *